(12) United States Patent
Hawkins et al.

(10) Patent No.: US 8,110,242 B2
(45) Date of Patent: Feb. 7, 2012

(54) METHODS OF PREPARING HYDROGEL COATINGS

(75) Inventors: Michael E. Hawkins, Columbia City, IN (US); Dirk L. Pletcher, Walkerton, IN (US); Brian Thomas, Columbia City, IN (US); Kai Zhang, Warsaw, IN (US); Hallie E. Brinkerhuff, Winona Lake, IN (US)

(73) Assignee: Zimmer, Inc., Warsaw, IN (US)

( * ) Notice: Subject to any disclaimer, the term of this patent is extended or adjusted under 35 U.S.C. 154(b) by 140 days.

(21) Appl. No.: 11/689,754

(22) Filed: Mar. 22, 2007

(65) Prior Publication Data

US 2007/0225823 A1    Sep. 27, 2007

Related U.S. Application Data

(60) Provisional application No. 60/785,906, filed on Mar. 24, 2006.

(51) Int. Cl.
*B05D 3/02* (2006.01)
*B05D 3/10* (2006.01)
*B05D 3/12* (2006.01)
*A61F 2/30* (2006.01)
*A61F 2/50* (2006.01)

(52) U.S. Cl. ....... 427/2.1; 427/2.24; 427/2.26; 427/307; 427/536; 427/569; 623/11.11; 623/16.11; 623/23.76

(58) Field of Classification Search .......... 427/2.1–2.24, 427/533, 535, 536, 569, 299, 307, 322; 623/11.11, 623/16.11–17.16, 18.11, 19.11–23.76
See application file for complete search history.

(56) References Cited

U.S. PATENT DOCUMENTS

| | | | |
|---|---|---|---|
| 3,200,178 | A | 8/1965 | Kanji |
| 3,862,265 | A | 1/1975 | Steinkamp |
| 3,875,302 | A | 4/1975 | Inoue |
| 4,036,788 | A | 7/1977 | Steckler |
| 4,058,491 | A | 11/1977 | Steckler |
| 4,060,678 | A | 11/1977 | Steckler |
| 4,071,508 | A | 1/1978 | Steckler |
| 4,279,795 | A | 7/1981 | Yamashita |

(Continued)

FOREIGN PATENT DOCUMENTS

EP    0256293    2/1988

(Continued)

OTHER PUBLICATIONS

Bryant, S.J. et al. "Crosslinking Density Influences Chrondrocyte Metabolism in Dynamically Leaded Photocrosslinked Poly(ethylene glycol) Hydrogels." Ann. Biomed. Eng., Mar. 2004, pp. 407-417, vol. 3, No. 3.

(Continued)

*Primary Examiner* — Timothy Meeks
*Assistant Examiner* — Cachet Sellman
(74) *Attorney, Agent, or Firm* — Cook Alex Ltd

(57) ABSTRACT

The present invention provides hydrogel coated, implantable medical devices and methods of coating hydrogels onto implantable medical devices. In one embodiment, a hydrogel coated medical device is formed by physically treating a surface of the medical device, chemically treating the surface, applying a hydrogel precursor and then crosslinking the hydrogel precursor to form a hydrogel coating on the surface of the medical device. The present invention may be particularly applicable for coating articulating surfaces on implantable medical devices such as artificial joints.

14 Claims, 1 Drawing Sheet

U.S. PATENT DOCUMENTS

| | | | |
|---|---|---|---|
| 4,300,820 A | 11/1981 | Shah | |
| 4,379,874 A | 4/1983 | Stoy | |
| 4,451,599 A | 5/1984 | Odorzynski | |
| 4,451,630 A | 5/1984 | Atkinson | |
| 4,464,438 A | 8/1984 | Lu | |
| 4,472,542 A | 9/1984 | Nambu | |
| 4,640,941 A | 2/1987 | Park | |
| 4,656,216 A | 4/1987 | Muller | |
| 4,663,358 A | 5/1987 | Hyon | |
| 4,664,857 A | 5/1987 | Nambu | |
| 4,699,146 A | 10/1987 | Sieverding | |
| 4,734,097 A | 3/1988 | Tanabe | |
| 4,771,089 A | 9/1988 | Ofstead | |
| 4,772,287 A | 9/1988 | Ray | |
| 4,808,353 A | 2/1989 | Nambu | |
| 4,842,597 A | 6/1989 | Brook | |
| 4,851,168 A | 7/1989 | Graiver | |
| 4,859,719 A | 8/1989 | Ofstead | |
| 4,871,490 A | 10/1989 | Rosiak | |
| 4,874,562 A | 10/1989 | Hyon | |
| 4,915,974 A | 4/1990 | D'Amelia | |
| 4,966,924 A | 10/1990 | Hyon | |
| 4,988,761 A | 1/1991 | Ikada | |
| 5,028,648 A | 7/1991 | Famili | |
| 5,047,055 A | 9/1991 | Bao | |
| 5,053,455 A | 10/1991 | Kroggel | |
| 5,106,876 A | 4/1992 | Kawamura | |
| 5,118,779 A | 6/1992 | Szycher | |
| 5,122,565 A | 6/1992 | George | |
| 5,157,093 A | 10/1992 | Harisiades | |
| 5,189,097 A | 2/1993 | LaFleur | |
| 5,192,326 A | 3/1993 | Bao | |
| 5,244,799 A | 9/1993 | Anderson | |
| 5,276,079 A | 1/1994 | Duan et al. | |
| 5,288,503 A | 2/1994 | Wood | |
| 5,306,311 A | 4/1994 | Stone | |
| 5,311,223 A | 5/1994 | Vanderlaan | |
| 5,315,478 A | 5/1994 | Cadwell | |
| 5,334,634 A | 8/1994 | Bastiolo | |
| 5,336,551 A | 8/1994 | Graiver et al. | |
| 5,358,525 A | 10/1994 | Fox | |
| 5,360,830 A | 11/1994 | Bastioli | |
| 5,362,803 A | 11/1994 | LaFleur | |
| 5,364,547 A | 11/1994 | Babb et al. | |
| 5,407,055 A | 4/1995 | Tanaka | |
| 5,409,966 A | 4/1995 | Duan et al. | |
| 5,410,016 A | 4/1995 | Hubbell | |
| 5,458,643 A | 10/1995 | Oka | |
| 5,527,271 A | 6/1996 | Shah | |
| 5,540,033 A | 7/1996 | Fox | |
| 5,552,096 A | 9/1996 | Auda | |
| 5,576,072 A * | 11/1996 | Hostettler et al. | 427/532 |
| 5,580,938 A | 12/1996 | Gutweiler | |
| 5,624,463 A | 4/1997 | Stone | |
| 5,632,774 A | 5/1997 | Babian | |
| 5,674,295 A | 10/1997 | Ray | |
| 5,681,300 A | 10/1997 | Ahr | |
| 5,705,296 A | 1/1998 | Kamauchi | |
| 5,709,854 A | 1/1998 | Griffith-Cima | |
| 5,711,960 A | 1/1998 | Shikinami | |
| 5,716,404 A | 2/1998 | Vacanti | |
| 5,723,331 A | 3/1998 | Tubo | |
| 5,834,029 A | 11/1998 | Bellamkonda | |
| 5,879,713 A | 3/1999 | Roth et al. | |
| 5,891,826 A | 4/1999 | Tsaur et al. | |
| 5,941,909 A | 8/1999 | Purkait | |
| 5,976,186 A | 11/1999 | Bao | |
| 5,981,826 A | 11/1999 | Ku | |
| 6,015,576 A | 1/2000 | See et al. | |
| 6,017,577 A | 1/2000 | Hostettler | |
| 6,040,493 A | 3/2000 | Cooke | |
| 6,080,488 A | 6/2000 | Hostettler | |
| 6,117,449 A | 9/2000 | See | |
| 6,120,904 A | 9/2000 | Hostettler | |
| 6,121,341 A | 9/2000 | Sawhney | |
| 6,129,761 A | 10/2000 | Hubbell | |
| 6,132,468 A | 10/2000 | Mansmann | |
| 6,139,963 A | 10/2000 | Fujii | |
| 6,146,686 A * | 11/2000 | Leitao | 427/2.27 |
| 6,156,345 A | 12/2000 | Chudzik | |
| 6,156,572 A | 12/2000 | Bettamkonda | |
| 6,162,456 A | 12/2000 | Dunbar | |
| 6,180,132 B1 | 1/2001 | Huang | |
| 6,180,606 B1 | 1/2001 | Chen | |
| 6,184,197 B1 | 2/2001 | Heinzman | |
| 6,187,048 B1 | 2/2001 | Milner | |
| 6,207,185 B1 | 3/2001 | See et al. | |
| 6,211,296 B1 | 4/2001 | Frate | |
| 6,224,893 B1 | 5/2001 | Langer | |
| 6,231,605 B1 | 5/2001 | Ku | |
| 6,232,406 B1 | 5/2001 | Stoy | |
| 6,238,691 B1 | 5/2001 | Huang | |
| 6,262,406 B1 | 5/2001 | Stoy | |
| 6,268,405 B1 | 7/2001 | Yao et al. | |
| 6,271,278 B1 | 8/2001 | Park et al. | |
| 6,280,475 B1 | 8/2001 | Bao et al. | |
| 6,306,424 B1 | 10/2001 | Vyakarnam | |
| 6,365,149 B2 | 4/2002 | Vyakarnam | |
| 6,371,984 B1 | 4/2002 | Van Dyke | |
| 6,372,283 B1 | 4/2002 | Shim | |
| 6,375,634 B1 | 4/2002 | Carroll | |
| 6,387,325 B1 | 5/2002 | Keusch | |
| 6,402,784 B1 | 6/2002 | Wardlaw | |
| 6,443,988 B2 | 9/2002 | Felt | |
| 6,509,098 B1 | 1/2003 | Merrill | |
| 6,531,147 B2 | 3/2003 | Sawhney | |
| 6,533,817 B1 | 3/2003 | Norton | |
| 6,583,219 B2 | 6/2003 | Won | |
| 6,602,952 B1 | 8/2003 | Bentley | |
| 6,608,117 B1 | 8/2003 | Gvozdic | |
| 6,620,196 B1 | 9/2003 | Trieu | |
| 6,626,945 B2 | 9/2003 | Simon | |
| 6,629,997 B2 | 10/2003 | Mansmann | |
| 6,630,457 B1 | 10/2003 | Aeschlimann | |
| 6,632,246 B1 | 10/2003 | Simon | |
| 6,645,517 B2 | 11/2003 | West | |
| 6,692,738 B2 | 2/2004 | MacLaughlin | |
| 6,706,690 B2 | 3/2004 | Reich | |
| 6,709,668 B2 | 3/2004 | Won | |
| 6,710,104 B2 | 3/2004 | Haraguchi | |
| 6,710,126 B1 | 3/2004 | Hirt | |
| 6,723,781 B1 | 4/2004 | Frate | |
| 6,730,298 B2 | 5/2004 | Griffith-Cima | |
| 6,733,533 B1 | 5/2004 | Lozier | |
| 6,780,840 B1 | 8/2004 | DeVore | |
| 6,783,546 B2 | 8/2004 | Zucherman | |
| 6,783,721 B2 | 8/2004 | Higham | |
| 6,783,793 B1 * | 8/2004 | Hossainy et al. | 427/2.25 |
| 6,803,420 B2 | 10/2004 | Cleary | |
| 6,852,772 B2 | 2/2005 | Muratoglu | |
| 6,855,743 B1 | 2/2005 | Gvozdic | |
| 6,861,067 B2 | 3/2005 | McGhee | |
| 7,235,592 B2 | 6/2007 | Muratoglu | |
| 7,531,000 B2 | 5/2009 | Hodorek | |
| 2001/0026810 A1 | 10/2001 | McGhee | |
| 2001/0032019 A1 | 10/2001 | Van Dyke | |
| 2001/0049417 A1 | 12/2001 | Frate | |
| 2001/0053897 A1 | 12/2001 | Frate et al. | |
| 2002/0022884 A1 | 2/2002 | Mansmann | |
| 2002/0026244 A1 | 2/2002 | Trieu | |
| 2002/0029083 A1 | 3/2002 | Zucherman | |
| 2002/0049498 A1 | 4/2002 | Yuksel | |
| 2002/0131952 A1 | 9/2002 | Hennink | |
| 2002/0151979 A1 | 10/2002 | Lambrecht | |
| 2002/0173855 A1 | 11/2002 | Mansmann | |
| 2002/0193531 A1 | 12/2002 | Stoy | |
| 2003/0008396 A1 | 1/2003 | Ku | |
| 2003/0065389 A1 | 4/2003 | Petersen | |
| 2003/0080465 A1 | 5/2003 | Higham | |
| 2003/0099709 A1 | 5/2003 | Shah | |
| 2003/0130427 A1 | 7/2003 | Cleary | |
| 2003/0152528 A1 | 8/2003 | Singh et al. | |
| 2003/0170308 A1 | 9/2003 | Cleary | |
| 2003/0195628 A1 | 10/2003 | Bao | |
| 2003/0232895 A1 | 12/2003 | Omidian | |
| 2003/0236323 A1 | 12/2003 | Ratner | |
| 2004/0002764 A1 | 1/2004 | Gainor | |

| | | | |
|---|---|---|---|
| 2004/0005423 A1 | 1/2004 | Dalton | |
| 2004/0030392 A1 | 2/2004 | Lambrecht | |
| 2004/0039447 A1 | 2/2004 | Simon | |
| 2004/0092653 A1 | 5/2004 | Ruberti | |
| 2004/0096509 A1 | 5/2004 | Hutchens | |
| 2004/0116641 A1 | 6/2004 | Mather | |
| 2004/0121951 A1 | 6/2004 | Rhee | |
| 2004/0127618 A1 | 7/2004 | Ulmer | |
| 2004/0127992 A1 | 7/2004 | Sehman et al. | |
| 2004/0131582 A1 | 7/2004 | Grinstaff et al. | |
| 2004/0131852 A1 | 7/2004 | Shimo et al. | |
| 2004/0133280 A1 | 7/2004 | Trieu | |
| 2004/0143329 A1 | 7/2004 | Ku | |
| 2004/0147673 A1 | 7/2004 | Calabro | |
| 2004/0153163 A1 | 8/2004 | Posner | |
| 2004/0161444 A1 | 8/2004 | Song | |
| 2004/0171740 A1 | 9/2004 | Ruberti | |
| 2004/0199250 A1* | 10/2004 | Fell | 623/14.12 |
| 2004/0220296 A1 | 11/2004 | Lowman | |
| 2004/0242770 A1 | 12/2004 | Feldstein | |
| 2004/0244978 A1 | 12/2004 | Shaarpour | |
| 2005/0004560 A1* | 1/2005 | Cox | 606/1 |
| 2005/0027069 A1 | 2/2005 | Rhee et al. | |
| 2005/0048103 A1 | 3/2005 | Cleary | |
| 2005/0049365 A1 | 3/2005 | Cleary | |
| 2005/0075454 A1 | 4/2005 | Plochocka et al. | |
| 2005/0095296 A1 | 5/2005 | Lowman | |
| 2005/0107561 A1 | 5/2005 | Lee et al. | |
| 2005/0197441 A1 | 9/2005 | Shibutani | |
| 2006/0078587 A1* | 4/2006 | Leong | 424/423 |
| 2006/0141002 A1* | 6/2006 | Liu et al. | 424/422 |
| 2006/0188487 A1 | 8/2006 | Thomas | |
| 2007/0004861 A1 | 1/2007 | Cai | |
| 2007/0202323 A1 | 8/2007 | Kleiner | |
| 2007/0293651 A1 | 12/2007 | Tada | |
| 2008/0090145 A1 | 4/2008 | Hiwara | |
| 2009/0053318 A1 | 2/2009 | Tan | |

FOREIGN PATENT DOCUMENTS

| | | |
|---|---|---|
| EP | 0290616 | 11/1988 |
| EP | 0365108 | 4/1990 |
| EP | 0505634 | 9/1992 |
| EP | 0696210 | 2/1996 |
| EP | 0738762 | 4/1996 |
| EP | 0784987 | 7/1997 |
| EP | 0835143 | 4/1998 |
| EP | 0845480 | 6/1998 |
| EP | 0927053 | 7/1999 |
| EP | 2338958 | 10/2000 |
| EP | 1079224 | 2/2001 |
| EP | 1174463 | 1/2002 |
| EP | 1593400 | 11/2005 |
| EP | 1595899 | 11/2005 |
| FR | 2786400 | 6/2000 |
| FR | 2865939 | 8/2005 |
| FR | 2865939 A1 | 8/2005 |
| FR | 2866571 | 8/2005 |
| JP | 01178545 | 7/1989 |
| JP | 01305959 | 12/1989 |
| JP | 03141957 | 6/1991 |
| JP | 04303444 | 10/1992 |
| JP | 09124730 | 5/1997 |
| JP | 09124731 | 5/1997 |
| JP | 10036524 | 2/1998 |
| JP | 10036534 | 2/1998 |
| JP | 10043286 | 2/1998 |
| JP | 10306534 | 2/1998 |
| WO | 9015082 | 12/1990 |
| WO | WO 94/13235 | 6/1994 |
| WO | 9417851 | 8/1994 |
| WO | WO 9502616 | 1/1995 |
| WO | 9526699 | 10/1995 |
| WO | 9640304 | 4/1998 |
| WO | 9817215 | 4/1998 |
| WO | 9853768 | 12/1998 |
| WO | 9903454 | 1/1999 |
| WO | 9913923 | 3/1999 |
| WO | 9907320 | 12/1999 |
| WO | WO 99/67320 A | 12/1999 |
| WO | 0117574 | 3/2001 |
| WO | WO 01/19283 | 3/2001 |
| WO | 0177197 | 10/2001 |
| WO | WO 02/04570 | 1/2002 |
| WO | 0213871 | 2/2002 |
| WO | 02060501 | 8/2002 |
| WO | 02087642 | 11/2002 |
| WO | 02087645 | 11/2002 |
| WO | 03008007 | 1/2003 |
| WO | 03074099 | 9/2003 |
| WO | WO 03/082359 | 10/2003 |
| WO | WO 03/082359 A | 10/2003 |
| WO | 040007651 | 1/2004 |
| WO | 04029174 | 4/2004 |
| WO | 2004031253 | 4/2004 |
| WO | 04047690 | 6/2004 |
| WO | 04055057 | 7/2004 |
| WO | 04060427 | 7/2004 |
| WO | 04063388 | 7/2004 |
| WO | 04066704 | 8/2004 |
| WO | 04072138 | 8/2004 |
| WO | 2004064693 | 8/2004 |
| WO | 2004069296 | 8/2004 |
| WO | 04093786 | 11/2004 |
| WO | 2005004943 | 1/2005 |
| WO | 2005035726 | 4/2005 |
| WO | WO 2005/030832 | 4/2005 |
| WO | WO 2005030382 | 4/2005 |
| WO | 2006021054 | 3/2006 |
| WO | 2006091706 | 8/2006 |
| WO | WO 2007/067697 A | 6/2007 |
| WO | 2007015208 | 8/2007 |
| WO | WO 2008/144514 | 11/2008 |
| WO | WO 2009/020793 A | 2/2009 |
| WO | WO 2009/032430 | 3/2009 |
| WO | WO 2009/088654 | 5/2010 |

OTHER PUBLICATIONS

Bryant, S.J. et al. "The Effects if Scaffold thickness on Tissue Engineered Cartilage in Photocrosslinked Poly (ethylene oxide) hydrogels." Biomaterials 22, 2001, pp. 619-628.

Bryant, S.J. et al. "Photocrosslinkable Poly(ethylene oxide) and Poly (vinyl alcohol) Hydrogels for Tissue Engineering Cartilage." 21st Annual Conference and the 1999 Annual Fall Meeting of the Biomedical Engineering Society, Oct. 13-15, 1999, Atlanta, GA; Engineering in Medicine and Biology 1999, p. 751, vol. 2.

Durmaz, S. et al. "Phase Separation during the Formation of Poly(acrylamide) Hydrogels" Polymer 41, 2000, pp. 5729-5735.

Gong, J.P. et al. "Friction of Polymer Gels and the Potential Application as Artificial Cartilage." SPIE, Mar. 1999, pp. 218-225, vol. 3669.

Guilherme, R. et al. "Hydrogels based on PAAm network with PNIPAAm included: hydrophilic-hydrophobic transition measured by the partition of Organe II and Methylene Blue in Water." Polymer 44, 2003, pp. 4213-4219.

Hassan, C.M. et al. "Modeling of Crystal Dissolution of Poly(vinyl alcohol) gels produced by freezing/thawing processes." Polymer 41, 2000, pp. 6729-6739.

Hassan, C.M. et al. "Structure and Morphology of Freeze/Thawed PVA Hydrogels," Macromolecules, 2000, pp. 2472-2479, vol. 33, No. 7.

Hickey, A.S. et al. "Solute Diffusion in Poly(vinyl) alcohol/poly(acrylic) acid composite membranes prepared by freezing/thawing techniques." J. Memb. Sci. 107, 1995, pp. 229-237.

Kobayashi, M. et al. "Development of an Artificial Meniscus Using Polyvinyl alcohol-hydrogel for early return to, and continuance of, athletic life in sportspersons with severe meniscus injury." ABSTRACT only, The Knee 10, 2003, p. 53.

Kobayashi, M. et al. "Preliminary Study of Polyvinylalcohol-hydrogel (PVA-H) artificial meniscus." Biomaterials 24, 2003, pp. 639-647.

Lester, C.L. et al. "Physical Properties of Hydrogels Synthesized from Lyotropic Liquid Crystalline Templates" Chem. Mater. 15, 2003, pp. 3376-3384.

Mano, V. et al. "Blends Composed of Poly(N-Isopropylacrylamide) and an Ethylene/Vinyl Alcohol Copolymer: Thermal and Morphological Studies" J. App. Polymer Sci., 2004, pp. 501-505.

Park, J.H. et al. "Hydrogels based on Poly(ethylene oxide) and poly (tetramethylene oxide) or poly)dimethyl siloxane). III. In vivo Biocompatability and Biostability." J. Biomed. Mater. Res. 64A, 2003, pp. 309-319.

Schmedlen, R.H. et al. "Photocrosslinkable polyvinyl alcohol hydrogels that can be modified with cell adhesion peptides for use in tissue engineering." Biomaterials, 23, 2002, pp. 4325-4332.

Suggs, L.J. et al. "In vitro Cytotoxicity and In Vivo Biocompatibility of Poly(propylene fumurate-co-ethylene glycol) hydrogels." J. Biomed. Mater. Res., 1999, pp. 22-32, vol. 46.

Thomas, J.D. "Novel Associated PVA/PVDP Hydrogels for Nucleuc Pulposus Replacement." Thesis, Master of Science in Material Engineering Degree, Drexel University, Sep. 2001.

Ushio, K. et al. "Attachment of Artificial Cartilage to Underlying Bone." J. Biomed. Mater. Res. Part B: Appl. Biomater. 68B, 2004, pp. 59-68.

Ushio, K. et al. "Partial Hemiarthroplasty for the treatment of Osteonecrosis of the Femoral Head: An Experimental Study in the Dog." J. Bone Joint Surg., 2003, pp. 922-930, vol. 85B.

Zhang, X. et al. "Synthesis and Characterization of Partially Biodegradable, Temperature and pH Sensitive Dex-MA/PNIPAAm Hydrogels." Biomat., 25, 2004, pp. 4719-4730.

"Lecture 7: Hydrogel Biomaterials: Structure and Physical Chemistry," Spring 2003, 8 pages.

ISR/WO for PCT/US2006/1006356 dated Jun. 22, 2006, 9 pages.

European Patent Office, International Search Report and Written Opinion received in corresponding PCT Application No. PCT/US2007/1064782 dated May 3, 2008, 10 pp.

N.A. Peppas, et al., Physicochemical Foundations and Structural Design of Hydrogels in Medicine and Biology, Annu. Rev. Biomed. Eng., 2000, 02:9-29.

Toru Moro, et al., Surface Grafting of Artificial Joints with Biocompatible Polymer for Preventing Periprosthetic Osteolysis, Nature Materials, vol. 3, Nov. 2004 (published online Oct. 24, 2004), pp. 829-836.

Christie M. Hassan, et al., Structure and Applications of Poly(vinyl alcohol) Hydrogels Produced by Conventional Crosslinking or by Freezing/Thawing Methods, Advances in Polymer Science, vol. 153, 2000, pp. 37-65.

EP Search Report for EP06255568.5, Jun. 15, 2007.

Noguchi et al., Poly(vinyl Alcohol) Hydrogel as an Artificial Articular Cartilage: Evaluation of Biocompatability. J. Applied Biomaterials, vol. 2, 101-107 (1991).

Rao et al. J. Chem. Soc. Dalton Trans., 2001, 1939-1944.

Anseth et al. "In situ forming degradable networks and their application in tissue engineering and drug delivery." J. Controlled Release 78 (2002), 199-209, 2002.

Lin-Gibson et al. "Synthesis and Characterization of PEG Dimethacrylates and Their Hydrogels." Biomacromolecules 2004, 5, 1280-1287, 2004.

Peppas et al. Structure and Applications of Poly(vinyl alcohol) Hydrogels Produced by Conventional Crosslinking or b Freezing/Thawing Methods. Adv. Polymer Sci. 153, 37 (2000).

LeGeros R. Z., "Calcium phosphates in oral biology and medicine," Monograph in Oral Science, vol. 15, pp. 1-201.

Chow et al.,"Octacalcium Phosphate," Monograph in Oral Science, vol. 18, pp. 94-112 and 130-148.

Li et al. Anal. Biochem., 256, 130-132 (1998).

Hassan et al. "Cellular PVA Hydrogels Produced by Freeze/Thawing." J. Appl. Poly. Sci. 76, 2075 (2000).

Carey et al., Adv. Org. Chem., Part B., p. 892, 2001.

Hickey et al. "Solute Diffusion in Poly(vinyl)alchohol/poly(acrylic acid) composite membranes prepared by freezing/thawing techniques." Polymer 38, pp. 5931-5936 (1997).

Wang B., et al. The Influence of Polymer concentration on the Radiation-chemical Yield of Intermolecular Crosslinking of Poly(Vinyl Alcohol) by gamma-rays in Deoxygenated Aqueous Solution. Radiation Physics and Chemistry, 2000. 59: p. 91-95.

Rosiak, J. M. & Ulanski, P. Synthesis of hydrogels by irradiation of polymers in aqueous solution, Radiation Physics and Chemistry 1999 55: 139-151.

Stammen, J. A., et al. Mechanical properties of a novel PVA hydrogel in shear and unconfined compression Biomaterials, 2001 22: p. 799-806.

Yamaura, K., et al. Properties of gels obtained by freezing/thawing of poly(vinyl alcohol)/water/dimethyl sulfoxide solutions. Journal of Applied Polymer Science 1989 37:2709-2718.

Lozinsky, V. I. and Damshkaln, L. G. Study of cryostructuration of polymer systems. XVII. Poly(vinyl alcohol) cryogels: Dynamics of cryotropic gel formation. Journal of Applied Polymer Science 2000 77:2017-2023.

Oka M et al. "Development of artificial articular cartilage," Pro. Inst. Mech. Eng. 2000 214:59-68.

EP Search Report for EP 06256525.4 dated May 20, 2007.

Babb et al. "Perfluorcyclobutane Aromatic Ether Polymers. III. Synthesis and . . . " J. Applied. Polymer Sci., vol. 69, (1998), pp. 2005-2012.

Glossary of Basic Terms in Polymer Science published by IUPAC, Pure Appl. Chem., 68, 2287-2311 (1996).

EP Search Report for EP06256452.1 dated May 23, 2007.

ISR/WO for PCT/US2006/046725 dated Jul. 28, 2008.

Park K.R. et al. "Synthesis of PVA/PVP Hydrogels having Two-Layer by Radiation and their Physical Properties." Rad. Phys. and Chem., Jun. 2003, pp. 361-365. vol. 67, No. 3-4.

Hassan C.M. "Diffusional Characteristics of Freeze/Thawed Poly(vinyl alcohol) hydrogels: Applications to protein controlled release from multilaminate devices." Eur. J. Pharm. and Biopharm., 2000, pp. 161-165, vol. 49.

Bass L.S. "Laser Tissue Welding: A Comprehensive Review of Current and Future Clinical Applications," Lasers in Surgery and Medicine, 1995, pp. 315-349. vol. 17.

Search Report for PCT/US2008/071435 dated Feb. 2, 2009.

ISR/WO for PCT/US20071064782 dated May 3, 2008.

ISR/WO for PCT/EP2005/010931 dated Feb. 16, 2006.

Carey et al., Adv. Org. Chem., Part B., p. 829, 2001.

Chow et al. "Octacalcium Phosphate," Monograph in Oral Science, vol. 18, pp. 94-111 and 130-147, (2001).

LeGeros R. Z., "Calcium Phosphates In Oral Biology and Medicine," Monograph in Oral Science, vol. 15, pp. 1-201, (1991).

Hickey et al., "Mesh Size and Diffusive Characteristics of Semicrystalline. . . ", Journal of Membrane Science 107 (1995) pp. 229-237.

Ushio, K., et al, "Partial Hemiarthroplasty for the treatment of osteoncrosis of the femoral head", Journal of Bone Joint Surgery., vol. 85B, pp. 922-930, 2003.

EP Search Report for EP Application No. 050010009.9-2115 dated Mar. 1, 2005.

EPO Invitation to Pay additional fees and Annex to Search Report for PCT/US2006/046725 dated Apr. 22, 2008, 8 pages.

Search Report and Written Opinion for PCT/US2008/071435 dated Feb. 5, 2009.

Preliminary Report on Patentability & Written Opinion for PCT/US2008/086817 dated Jul. 6, 2010.

Search Report and Written Opinion for PCT/US2008/083213 dated May 8, 2009.

Preliminary Report on Patentability & Written Opinion for PCT/US2008/071539 dated Mar. 2, 2010.

Preliminary Report on Patentability and Written Opinion for PCT/US2006/006356 dated Aug. 28, 2007.

Taguchi, Chemistry Letters, 711-712 (1998).

Lu et al., Journal of Controlled Release, 57,291-300 (1999).

West et al., Reactive Polymers, 139-147 (1995).

Green et al., Organic Chemistry Principles and Industrial Practice, Wiley VCH 2003.

Tripathy et al., "Novel Flocculating Agebt Based on Sodium Alginate and Acrylamide." European Polymer Journal, 35, 2057-2072 (1999).

Haralabakopoulus et al., J. Appl. Poly. Sci., 69, 1885-1890, (1998).

International Preliminary Report on Patentability for PCT/US2008/071435, (2008).

International Preliminary Report on Patentability for PCT/US2008/071539, (2008).

Bray, J.C. et al. "Poly(vinyl Alcohool) Hydrogels: Formation by Eelctron Beam Irradiation of Aqueous Solutions and Subsequent Crystallization." J. Applied Polymer Sci., vol. 17, pp. 3779-3794, 1973.

Bray, J.C. et al. "Poly(vinyl Alcohol) Hydrogels for Synthetic Articular Cartilage Material," Biomed. Mater. Res., vol. 7, pp. 431-443, 1973.

Kawanishi, K. Thermodynamic Consideration of the Sol-Gel Transition in Polymer Solutions. 35th Annual Meeting of the Society of Polymer Science, Japan 1986.

Lozinsky, V.I. et al. "Study of Cryostructures of Polymer Systems, XIV. Poly(vinyl alchohol) Cryogels: Apparent Yield of Freeze-Thaw Induced Gelation of Concentrated Aqueous Solutions of the Polymer." J. Applied Polymer Sci., vol. 77, 1822,1831 (2000).

Lozinsky, V.I. et al. "Study of Cryostructuration of Polymer Systems, XVII. Poly(vinyl alcohol) Cryogels: Dynamics of the Cryotropic Gel Formation." J. Appl. Polymer Sci., vol. 77, 2017-2023 (2000).

Lozinsky, V.I. et al. "Swelling Behavior of poly (vinyl alcohol) cryogels employed as matrices for cell immobilization." Enzyme Microb. Technol., vol. 18.

Peppas et al. "Reinforced Uncrosslinkable Poly (vinyl alcohol) gels produced by cyclic freezing-thawing processes: A Short Review." J. Controlled Release, 16 (1991), 305-310.

Mondino, A.V. et al. "Physical properties of gamma irradiated poly (vinyl alcohol) hydrogel preparations" Radiation Physics and chemistry, 55, p. 723,726 (1999).

Urushizaki, F. Swelling and Mechanical Properties of Poly (vinyl alcohol) Hydrogels. Intl. J. Pharma., 58, 135-142, 1990.

Lozinsky, V.I. "On the Possibility of Mechanodestruction of Poly (vinyl Alcohol) Molecules under Moderate Freezing of its Concentrated Water Solutions." Polymer Bulletin, 15, p. 333-340 (1986).

Yokoyama, F. "Morphology and Structure of Highly Elastic Poly (vinyl alcohol) Hydrogel Prepared by Repeated Freezing-and-Melting" Colloid & Polymer Sci. 264, 595-601 (1986).

Covert, R.J. et al. "Friction and Wear Testing of a New Biomaterial for Use as an Articular Cartilage Substitute," BED 50 (2001), 355-356, Bioengineering Conference, ASME 2001.

Ding, Mei Yee. Characterisation of Polyvinyl Alcohol Hydrogels, 2003. Undergraduate Chemical Engineering Thesis, University of Queensland, Brisbane QLD 4072, Australia http://www.cheque.uq.edu.au/ugrad/theses/2003/pdf/CHEE4006/40054522/40054522.pdf (working link on 04/20/1009).

Jaguar-Grodzinski, J. "Biomedical Application of Functional Polymers." Reactive and Functional Polymers 39 (1999) 99-138.

Ulanski, P. et al. "OH-Radical induced crosslinking and strand breakage of poly (vinyl alcohol) in aqueous solution in the absence and presence of oxygen. A pulse radiolysis and product study" Macromol. Chem. Phys. 195, p. 1443-14461 (1994).

EP Communication for EP Application No. 07 759 243.4 dated Apr. 15, 2011.

English Language Abstract of FR 2865939(A1), (2005).

* cited by examiner

METHODS OF PREPARING HYDROGEL COATINGS

RELATED APPLICATION

Pursuant to 37 C.F.R. §1.78(a)(4), this application claims the benefit of and priority to prior filed co-pending Provisional Application Ser. No. 60/785,906, filed Mar. 24, 2006, which is expressly incorporated herein by reference.

FIELD OF THE INVENTION

The present invention relates generally to methods of coating an implantable device and specifically, methods of coating an articulating surface on an implantable device with a hydrogel material.

BACKGROUND

Osteolysis, or bone loss, in the vicinity of an orthopedic implant induced by the wear debris from implant devices is a significant challenge for patients with orthopedic implants and for clinicians treating these patients.

Attempts have been made to reduce the production of wear debris from implanted devices by coating articulating portions and/or other wear-prone portions of these devices to reduce friction. For example, biocompatible phospholipid polymers, such as 2-methacryloyloxyethyl phosphorylcholine (MPC), have been coated onto implants in an attempt to decrease friction between contacting device portions and, thus, reduce the production of wear debris. Moro, et. al., "*Surface Grafting of Artificial Joints with a Biocompatible Polymer for Preventing Periprosthetic Osteolysis,*" *Nature Materials*, 3, 829 (2004).

Hydrogels have shown promise for use in a variety of implantable devices and materials due, in part, to the biocompatibility and durability of materials formed from hydrogels. Additionally, hydrogel materials may exhibit rubbery and pliable behaviors, and/or have highly lubricious surfaces. An overview of considerations for biological and medical applications of hydrogels can be found in Peppas, et al., *Ann. Rev. Biomed. Eng.* 2, 9 (2000), which is incorporated by reference in its entirety.

Because of these properties, hydrogels are considered excellent lubricants for coating onto implantable medical devices. Unfortunately, hydrogels do not adhere well to certain metal, polymer and/or ceramic materials commonly used to manufacture implantable devices, and therefore, hydrogels may be difficult to coat onto the surfaces of such materials.

SUMMARY OF THE INVENTION

In one embodiment, the present invention provides a method for coating an implantable medical device by (1) physically treating a surface of the device to form physical bonding sites, (2) chemically treating the same surface to form chemical bonding sites, (3) applying a hydrogel precursor to the surface, and (4) crosslinking the hydrogel precursor to form a hydrogel coating on the surface.

In another embodiment, the present invention provides an implantable medical device including at least a first articulating surface that is coated with a hydrogel.

DETAILED DESCRIPTION

Figure 1:
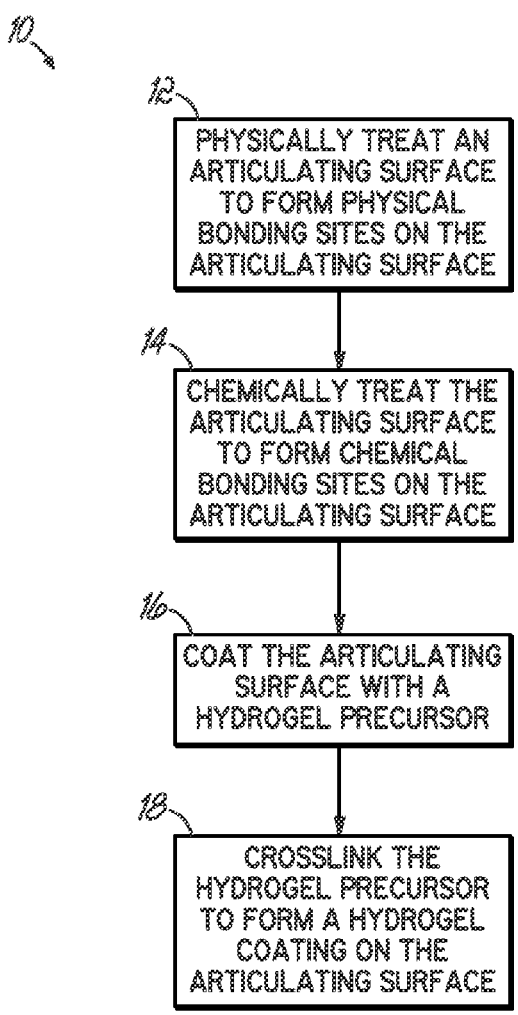
FIG. 1 shows a flow-chart illustrating a method of coating an implantable medical device with a hydrogel according to an embodiment of the present invention.

FIG. 1 is a flow-chart summarizing a method 10 of coating a hydrogel on an articulating surface of an implantable medical device. The invention generally includes the steps of physically treating the articulating surface to form physical bonding sites on the articulating surface (block 12), chemically treating the articulating surface to form chemical bonding sites on the articulating surface (block 14), coating the articulating surface with a hydrogel precursor (block 16), and crosslinking the hydrogel precursor to form a hydrogel coating on the articulating surface (block 18). Each of these steps and components used in the method of the invention is described in detail below.

As used herein, the term "articulating surface" refers to a surface of an implantable medical device that moves with respect to, and contacts, a second surface of the medical device, an adjacent medical device, or an endogenous tissue surface. An example of an implantable medical device with an articulating surface is an artificial hip joint replacement. These devices may include a ball and socket joint, much like a natural hip joint. The respective surfaces of the ball and the socket are examples of articulating surfaces that may be treated according to embodiments of the present invention. In alternate embodiments, the surface need not be an articulating surface, but rather any surface for which wear debris is a concern.

The medical devices and their surface(s), including articulating surfaces, may be formed from a variety of suitable materials, including polymer, metal, and ceramic materials as well as combinations and/or composites of the foregoing. Examples of suitable polymer materials that may form a medical device and/or an articulating surface include a variety of polyolefins, including ultra high molecular weight polyethylene (UHMWPE) which may be cross-linked chemically or by irradiation, polyetherketones (e.g., polyetheretherketone (PEEK) and polyetherketoneketone (PEKK)) and derivatives and blends thereof. Other suitable polymers may include thermoplastic polyurethanes (TPU), polyesters such as polyethylene terephthalate (PET), nylon polymers such as nylon-11 and nylon-12, block copolymers of polyether and polyester polymers (for example various HYTREL® block copolymers (available from DuPONT), block copolymers of polyether polymers and polyamides (for example, PEBAX® resin series, available from ATOCHEM), polyimides, polyolefins such as polyethylenes (PE) and polypropylenes (PP), synthetic rubbers, including SBR and EPDM, thermoplastic hydrocarbon polymers (KRATON®, available from SHELL, and other similar commercial products from other sources), as well as natural rubber.

Suitable metallic materials include stainless steel, titanium, nickel, tantalum, molybdenum, cobalt, chromium, nitinol (nickel-titanium alloy), and VITALLIUM® (cobalt-chromium alloy) as well as combinations, composites and alloys (e.g., $TiAl_6V_4$) of the foregoing. Ceramic materials such as alumina and zirconia may also be used to form the medical device and/or articulating surface.

If the articulating surface is formed of a moldable polymer, the polymer may be consolidated and/or compressed into suitable form for use as (or as part of) a prosthetic device or other implant. Suitable compression and/or consolidation techniques include, for example, compression molding, direct compression molding, hot isostatic pressing, ram extrusion, high-pressure crystallization, injection molding, sintering, casting or other conventional methods of compressing and/or consolidating the polymer. If desired, the compressed/consolidated polymer may be further processed or manufactured by milling, machining, drilling, cutting, assembling with other components, and/or other manufacturing or pre-manufacturing steps conventionally employed to manufacture implants from a polymer. One example of a suitable polymer that may be consolidated and/or compressed is UHMWPE.

Physical Bonding Sites

In one embodiment of the present invention, physical bonding sites are formed on an articulating surface of an implantable medical device. In one embodiment, physical bonding sites are formed by physically treating the articulating surface by, for example, roughening and/or patterning the surface with solid particles and/or employing known wet or dry etching techniques to impart a texture or other topography onto the articulating surface. These physical bonding sites may improve the physical bonding or adhesion between the articulating surface and the hydrogel.

Suitable particulate material for roughening the articulating surface include salts, sugars, sodium bicarbonate, calcium carbonate, aluminum oxide, calcium borate, hydroxyapatite, calcium phosphate, and particulate glass. Etching may be accomplished by pattern-wise exposing the articulating surface to energy such as ultraviolet, visible, infrared or heat energy. Alternatively or additionally, the articulating surface may be pattern-wise exposed to a wet etchant or developer known in the art to remove portions of the articulating surface. Suitable wet etchants include acidic materials, alkaline materials and metal silicates. The surface may also be patterned using techniques typically performed to create microelectronic devices.

In another embodiment, physical bonding sites are molded into the articulating surface of the implant. Any type of suitable molding techniques may be used. Examples of these include injection molding or compression molding using porogens such as salt particles or supercritical fluids. In further examples, physical bonding sites may be formed in a manner widely used in the semiconductor and microelectromechanical systems industries, including devices such as the microgripper technology.

Figure 2A:
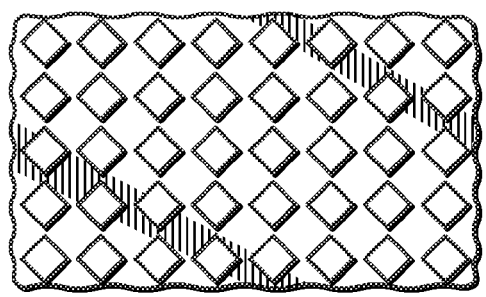
FIG. 2A shows a top view of a surface of an implantable medical device after performing a physical treatment according to embodiments of the present invention.
Figure 2B:
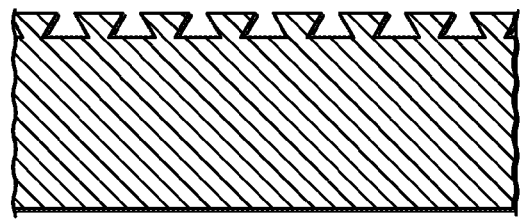
FIG. 2B shows a cross-sectional view of a surface of an implantable medical device after performing a physical treatment according to embodiments of the present invention.

The resulting pattern, texture and/or other topography formed on the articulating surface may encourage physical bonding (e.g. mechanical interlocking, physical adhesion and/or friction interaction) between the hydrogel coating and the articulating surface. An example of a suitable pattern is a "dovetail" pattern and is illustrated in the top view of FIG. 2A and the cross-sectional view of FIG. 2B.

The articulating surfaces may further be subjected to an annealing process. The term "annealing" refers to heating a material below its peak melting point in order to strengthen and relieve stress on the polymer, particularly those attributable to creating the physical bonding sites. Annealing time can be at least 1 minute to several weeks long. In one embodiment, the annealing time is about 4 hours to about 48 hours. In another embodiment, the annealing time is about 24 hours to about 48 hours. In another embodiment, the annealing time is about 24 hours. The annealing time required to achieve a desired level of recovery following mechanical deformation is usually longer at lower annealing temperatures. "Annealing temperature" refers to the thermal condition for annealing in accordance with the invention. For example, a polymeric material may be annealed at a temperature of up to about 200° C. for up to about 72 hours, more particularly at about 150° C. for about 5 hours. Alternatively or additionally, a polymer may be subjected to the mechanical annealing processes reported in U.S. Pat. No. 6,852,772 to Muratoglu. In one embodiment, however, no annealing treatments are performed.

Chemical Bonding Sites

In one embodiment of the present invention, chemical bonding sites are formed on the articulating surface of the implantable medical device. This step is typically performed after forming physical bonding sites, although it could be performed before the physical bonding sites are formed as well. Chemical bonding sites differ from the physical bonding sites in that they promote chemical bonding, such as covalent bonds, ionic bonds and/or hydrogen bonds between the articulating surface and the hydrogel coating. The type of chemical bonding sites and the method by which they are formed depends upon the desired hydrogel coating and the material that forms the articulating surface.

In one embodiment, the chemical bonding sites are formed by plasma coating the articulating surface. Suitable methods of plasma coating are known in the art. For example, U.S. Pat. No. 6,120,904 to Hostettler et al., which is hereby incorporated by reference, describes a method of plasma coating a medical implant.

In one embodiment, primary and/or secondary amino groups are fixed on the articulating surface of the implantable medical device. The first step of the method of plasma coating involves either a chemical oxidation treatment or exposing the articulating surface to oxygen-containing gases, optionally in the presence of argon (Ar) and/or other inert gases, to generate free radicals. The second step involves exposing the articulating surface to plasma gases containing nitrogen atoms to form the amino groups. Suitable plasma gases that contain nitrogen atoms include ammonia, primary and secondary amines, nitrous oxide, nitrogen, other gases containing nitrogen moieties, and mixtures of such gaseous compounds. The result of these two steps is a surface that is hydrophilic and contains reactive amino groups that are capable of forming bonds with the functional groups of hydrogel precursors.

In another embodiment, the chemical bonding sites are formed by grafting or coating polymers, oligomers, or macromers having desired functional groups onto the articulating surface. Examples of suitable polymers that may be used to form the chemical bonding sites according to the present invention include polyethylene-co-vinyl alcohol, polyvinyl alcohol, polyethylene glycol, polyethylene oxide and polyacrylamide. These materials can be applied as a primer coating after physically treating the surface, to form chemical bonding with both the surface (e.g., UHMWPE) and the hydrogel coating (e.g., PVA).

In another embodiment that may be particularly applicable to metal articulating surfaces, the chemical bonding sites are formed by applying either acids or bases to the articulating surface to create chemical moieties such as hydroxyl groups, acid groups or nitrates, which generate chemical bonding sites on the articulating surface. Examples of suitable acids include hydrochloric acid (HCl), nitric acid ($HNO_3$), sulfuric acid ($H_2SO_4$), and hydrofluoric acid (HF). An example of a suitable base is sodium hydroxide (NaOH). In another example, hydroxyl groups can be formed on the surface of a chrome-containing metal device using a sulfuric acid/peroxide treatment. The hydroxyl groups formed on the metal surface by this treatment encourages chemical bonding of organic molecules to the metal surface.

In certain embodiments, it may be desirable to render the articulating surface more hydrophilic before forming chemical bonding sites as described above. In one embodiment, the surface is first treated with a plasma gas containing oxygen, either as pure oxygen, or as air, water vapor, or mixtures thereof. According to methods known in the art, the oxygen-containing plasma treatment step affixes hydroxyl groups, carbonyl groups, carboxyl groups, and mixtures thereof to the surface, thereby rendering the surface more polar and hydrophilic. Another embodiment involves chemically treating the surface material with oxidative reagents such as oxygen, ozone, peroxides, hydrogen peroxide, oxygen-fluorine or air-fluorine mixtures, or peroxygen acids. The oxygen plasma treatment is then followed by a plasma treatment step with a nitrogen-containing gas to affix highly reactive primary or secondary amino groups onto the surface.

In another embodiment, a non-reducing plasma gas, such as argon, or argon and ammonia, is first applied to the surface to make the surface more polar and hydrophilic while creating free radicals on the surface. This step is followed immediately by applying a gaseous non-plasma post-stream of ammonia, organic amines in the gaseous state, or mixtures thereof, to affix highly reactive primary or secondary amino groups onto the surface. Alternatively, the second non-plasma step can be substituted by a plasma-treatment step whereby the nitrogen-containing gases are subjected to radio or microwave frequency plasma discharge.

The articulating surface may also be washed with polar or nonpolar solvents prior to chemical treatment to remove any surface impurities such as lubricants, antioxidants, plasticization agents, release agents, and/or particles from the physical treatment. These impurities may also result from the initial polymer manufacturing processes or from plastic forming techniques. Examples of suitable solvents which may be used for this purpose include alcohols such as methanol, ethanol, and isopropanol; ketones such as acetone and methylethyl ketone; chlorinated hydrocarbons such as methylene chloride and 1,1,1-trichloroethane; hydrocarbons such as pentanes, n-hexane, and petroleum ethers; other cleaning spirits; and ethers such as diisopropyl ether, dioxane, tetrahydrofuran; and mixtures of any suitable solvents. If non-flammable cleaning solvents are used, the removal of surface impurities can be carried out by means of vapor degreasers, a procedure known in the art. Aqueous solutions of nonionic, anionic, and cationic surfactants may also be used as washing fluids, if desired, followed by rinsing with water or distilled water to remove surface impurities that can interfere with the plasma treatment. Impurities on the articulating surface may detract from the formation of cohesive bonds with the hydrogels later in the process.

After chemical treatment and prior to coating, it may be necessary to preserve the chemical bonding sites in a controlled environment. For example, if hydroxyl groups are formed on the surface of a device, it may be necessary or desirable to store the device in deionized water until the coating treatment is performed.

Coating with Hydrogel Precursor

Once the articulating surface of the implantable medical device contains suitable physical bonding sites and chemical bonding sites, a hydrogel precursor is coated onto the articulating surface of the device. Hydrogel precursors refer to the hydrophilic monomers, homopolymers or copolymers that may be applied to the articulating surface in solution before crosslinking to form a hydrogel coating.

Examples of suitable hydrogel precursors for use in this step include polyvinyl alcohol, polyglycols such as polyethylene glycol dimethacrylate, polyethylene glycol diacrylate, polyhydroxyethyl methacrylate, polyvinyl pyrrolidone, polyacrylamide, polyacrylic acid, hydrolyzed polyacrylonitrile, polyethyleneimine, ethoxylated polyethyleneimine polyallylamine, and polyglycols as well as monomers, oligomers, macromers, copolymers and/or other derivatives of the foregoing. Other suitable hydrogel precursors include anionic polymers such as hyaluronic acid, cationic polymers such as chitosan, amphipathic polymers such as collagen, gelatin and fibrin, and neutral polymers such as dextran and agarose. Interpenetrating polymer networks (e.g. combinations of water soluble polymers and water insoluble precursors) and polymers having backbones modified with calcium or phosphate derivatives may also be suitable for use in certain embodiments.

In one embodiment, the hydrogel precursor is polyvinyl alcohol or a derivative thereof. Polyvinyl alcohol (PVA) may be produced by free-radical polymerization of vinyl acetate to form polyvinyl acetate, followed by hydrolysis to yield PVA. The hydrolysis reaction does not go to completion, which leaves pendent acetate groups at some points along the polymer chain. The extent of the hydrolysis reaction determines the degree of hydrolysis of the PVA. Commercially available PVA can have a degree of hydrolysis over 98% in some cases.

In another embodiment, the hydrogel precursor is a blend of polymers that includes a hydrophilic polymer and a second polymer having hydrophobic character and hydrophilic character. The hydrophilic polymer may be polyvinyl alcohol, for example. Additional suitable hydrophilic polymers that may be used in the blends include polyhydroxyethyl methacrylate, polyvinyl pyrrolidone, polyacrylamide, polyacrylic acid, hydrolyzed polyacrylonitrile, polyethyleneimine, ethoxylated polyethyleneimine, polyallylamine, and polyglycols.

In a further embodiment, the hydrogel precursor is a blend of polyvinyl alcohol and a second polymer having hydrophobic recurring units and hydrophilic recurring units. The second polymer may be a copolymer such as polyethylene-co-vinyl alcohol, for example. In some embodiments, the hydrogel precursor is a thermoplastic.

In another embodiment, the hydrogel precursor includes hydrophilic polyurethane derived from water-soluble polyether polyols and organic polyisocyanates. In one embodiment, the polyisocyanates include aliphatic, cycloaliphatic, aralphatic, and heterocyclic polyisocyanates containing aliphatically attached terminal isocyanate groups. These groups may react with amino groups. Therefore, if these hydrogel precursors are used, plasma treatment resulting in primary and secondary amino groups may be a particularly suitable method for forming chemical bonding sites on the articulating surface.

To speed up the process of coating the hydrogel onto the articulating surface, the implantable medical device coated with the hydrogel precursors may be heated from about 40° C. up to about 70° C., or higher, to speed the formation of cohesive bonds with slower reacting chemical functional groups such as urethane, urea, amide, carboxyl, and hydroxyl groups that are either present in the polymer of the articulating surface, or have been affixed to the articulating surface in the previously described step.

The hydrogel precursor may be combined with a suitable carrier prior to application to the articulating surface. Suitable carriers include water, organic solvents, or mixtures thereof, as well as other plasticizers and diluents. Examples of suitable carriers include water, dimethyl sulfoxide (DMSO), polar glycerine, ethylene glycol, propylene glycol, ethanol, tetrahydrofuran, toluene, dimethylformamide, dimethylacetamide, acetone, acetonitrile, cyclohexane, cyclopentane, 1,4-dioxane, ethyl acetate, glyme, methyl tert-butyl ether, methyl ethyl ketone, pyridine, and chlorobenzene. The mixture of hydrogel precursor and carrier may be applied to the articulating surface in any known manner, including spraying, brushing, dipping, molding or electrodeposition techniques.

The hydrogel precursors may also include or be combined with additional polymers, or conventional additives such as plasticizers, components for inhibiting or reducing crack formation or propagation, components for inhibiting or reducing creep, or particulates or other additives for imparting radiopacity to the material. By way of example only, an additive for imparting radiopacity can include metal oxides, metal phosphates, and metal sulfates such as barium sulfate, barium titanate, zirconium oxide, ytterbium fluoride, barium phosphate, and ytterbium oxide.

In certain embodiments, additional bioactive agents may be incorporated into the mixture of hydrogel precursors and the carrier prior to applying the mixture to the articulating surface. Examples of suitable bioactive agents include, without limitation, proteins such as BMPs, growth factors, pharmaceuticals such as analgesics or antibiotics, enzymes and/or genes.

Crosslinking

After applying the hydrogel precursors onto the articulating surface, the precursors are crosslinked to form a hydrogel coating. Examples of suitable crosslinking techniques include radiation crosslinking, physical crosslinking and chemical crosslinking.

In one embodiment of the present invention, crosslinking is achieved by irradiation. This method includes exposing hydrogel precursors to an irradiating beam such as ultraviolet or blue light, collectively referred to herein as "UV/Vis radiation". In this embodiment, a photoinitiator such as an IRGACURE brand initiator (Ciba Specialty Chemicals) may be combined with the hydrogel precursors, or with one of the mixtures used to form the hydrogel precursors. In one embodiment, UV/Vis radiation sources may be operable at a wavelength of approximately 365 nm and an energy level of 300 $\mu W/cm^2$.

In certain embodiments, the radiation source is electron beam radiation. Electron beam radiation exposure may be performed using conventionally available electron beam accelerators. One commercial source for such an accelerator is IBA Technologies Group (Belgium). Suitable accelerators may produce an electron beam energy between about 2 to about 50 MeV. In one embodiment, the electron beam energy is about 10 MeV. Electron beam exposure may be carried out in a generally inert atmosphere, including for example, an argon, nitrogen, vacuum, or oxygen scavenger atmosphere. Exposure may also be carried out in air under ambient conditions. Gamma and x-ray radiation may be suitable for use in alternate embodiments.

In another embodiment, physical crosslinking may be employed in the crosslinking step. Physical crosslinking may be achieved by the freeze-thaw solution-phase methods described below, for example, or by conventional freeze-thaw techniques known in the art of PVA hydrogels. Such methods are described in known scientific literature, including Peppas, et al., *Adv. Polymer Sci.* 153, 37 (2000) and the references cited therein. Freeze-thaw methods are thought to cause hydrogen bonding between the hydrophilic groups of the polymers. One advantage of a freeze-thaw method of crosslinking is that it permits the water-swellable material to be manufactured without the use of potentially toxic solvents or chemical crosslinking agents, initiators, and the like.

In still another embodiment, chemical crosslinking methods may be used. Examples of suitable chemical crosslinking agents include monoaldehydes such as formaldehyde, acetaldehyde, or glutaraldehyde in the presence of a solvent such as sulfuric or acetic acid or methanol. Other suitable crosslinking agents include diisocyanate compounds, which can result in urethane linkages, or epoxy compounds.

Crosslinking achieved using enzymes such as a calcium independent microbial transglutaminase, which catalyzes transamidation reactions to form N-ϵ-(γ-glutamyl)lysine crosslinks in proteins, may also be suitable as a type of chemical crosslinking according to embodiments of the present invention.

A combination of different crosslinking steps may be performed in the practice of the present invention. For example, a freeze-thaw cycle could be used to provide physical crosslinking, followed by electron-beam or gamma irradiation to provide more complete crosslinking. As other examples, chemical crosslinking could be followed by electron-beam or gamma irradiation, or a freeze-thaw step could be performed after crosslinking by any of chemical, electron-beam or gamma irradiation. A combination of crosslinking approaches may be suitable for providing additional strength or resilience to the resulting hydrogel.

A variety of implants, and in particular endoprosthetic joint replacements having articulating surfaces, may be prepared by employing the methods reported herein. Examples of such implants include artificial hips and knees, cups or liners for artificial hips and knees, spinal replacement disks, artificial shoulder, elbow, foot, ankle and finger joints, mandibles, and bearings of artificial hearts.

What is claimed is:

1. A method of coating an implantable medical device comprising:
    physically treating a surface of the device to form physical bonding sites;
    chemically treating the surface of the medical device to form chemical bonding sites;
    coating the surface with a single type of hydrogel precursor; and
    crosslinking the hydrogel precursor to form a hydrogel coating on the surface bonded thereto by the physical and chemical bonding sites, and wherein the surface of the medical device is an articulating surface.

2. The method of claim 1, wherein the surface is a polymer, metal, ceramic, combinations, composites or alloys thereof.

3. The method of claim 1, wherein physically treating the surface comprises at least one of roughening the surface with solid particles, etching the surface, or molding the surface to form a pattern, texture or topography on the surface.

4. The method of claim 1, wherein physically treating the surface comprises roughening the surface with solid particles selected from the group consisting of salts, sugars, sodium bicarbonate, calcium carbonate, aluminum oxide, calcium borate, hydroxyapatite, calcium phosphate, particulate glass, and combinations thereof.

5. The method of claim 1, wherein chemically treating the surface comprises at least one plasma treating the surface; grafting materials having functional groups onto the surface; treating the surface with an acid, base or an oxidant; or combinations thereof.

6. The method of claim 1, wherein chemically treating the surface comprises plasma treating by exposing the surface to plasma gas containing oxygen, nitrogen, argon, ammonia, or combinations thereof.

7. The method of claim 1, further comprising washing the surface with a solvent or a surfactant, or a combination thereof, prior to chemically treating.

8. The method of claim 1, further comprising annealing the physically treated surface prior to coating.

9. The method of claim 1, wherein the coating the surface with the single type of hydrogel precursor further comprises heating the implantable medical device.

10. The method of claim 1, wherein the single type of hydrogel precursor is a polyvinyl alcohol.

11. The method of claim 1, wherein crosslinking the hydrogel precursor comprises radiation crosslinking, physical crosslinking, chemical crosslinking, or combinations thereof.

12. The method of claim 11, wherein crosslinking the hydrogel precursor includes radiation crosslinking by exposing the hydrogel precursor to at least one of ultraviolet radiation, electron beam radiation, gamma radiation, or x-ray radiation.

13. The method of claim 11, wherein crosslinking the hydrogel precursor includes physical crosslinking by exposing the hydrogel precursor to freezing and thawing.

14. The method of claim 11, wherein crosslinking the hydrogel precursor includes chemical crosslinking by exposing the hydrogel precursor to a monoaldehyde or a diisocyanate.

* * * * *